US011250959B2

(12) United States Patent
Brown et al.

(10) Patent No.: US 11,250,959 B2
(45) Date of Patent: *Feb. 15, 2022

(54) DYNAMICALLY UPDATING A COMMUNITY EARLY WARNING SCORE

(71) Applicant: CERNER INNOVATION, INC., Kansas City, KS (US)

(72) Inventors: Georgia Brown, Kansas City, KS (US); Sheila Farley, Kansas City, KS (US); Stacey Brown, Kansas City, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 219 days.

This patent is subject to a terminal disclaimer.

(21) Appl. No.: 16/236,835

(22) Filed: Dec. 31, 2018

(65) Prior Publication Data

US 2020/0111547 A1 Apr. 9, 2020

Related U.S. Application Data

(60) Provisional application No. 62/742,754, filed on Oct. 8, 2018.

(51) Int. Cl.
*G16H 80/00* (2018.01)
*G16H 40/20* (2018.01)
(Continued)

(52) U.S. Cl.
CPC ........... *G16H 80/00* (2018.01); *G06F 16/951* (2019.01); *G16H 10/60* (2018.01); *G16H 40/20* (2018.01); *G16H 50/30* (2018.01)

(58) Field of Classification Search
CPC ........ G16H 80/00; G16H 50/30; G16H 40/20; G16H 10/60; G06F 16/951
See application file for complete search history.

(56) References Cited

U.S. PATENT DOCUMENTS

2009/0216556 A1 8/2009 Martin et al.
2014/0019149 A1 1/2014 Yu et al.
(Continued)

FOREIGN PATENT DOCUMENTS

CN 109036500 A * 12/2018

OTHER PUBLICATIONS

Industry Roundtable: Patient Monitoring: FET convened an Industry roundtable of experts to discuss issues in the patient monitoring market, such as alarm fatigue, pediatric sensors, and data security RT for Decision Makers in Respiratory Care: 16(2). Anthem Systems LLC. (May 2018-Jun. 2018)) (Year: 2018).*

(Continued)

*Primary Examiner* — Linh Giang Le
(74) *Attorney, Agent, or Firm* — Shook, Hardy & Bacon L.L.P.

(57) ABSTRACT

Embodiments of the present disclosure relate to systems, methods, and user interfaces for providing intelligent touch care. More particularly, embodiments of the present disclosure utilizes contributing data elements in a community early warning score (CEWS) to predict touchpoint discipline and to recommend frequency, modality, and upstream transitions of care and outside service referrals for a patient in a community care setting. In response to a touch point (e.g., a change in condition or medication, a scheduled or unscheduled appointment, or a patient question), the CEWS can be utilized along with data in an EHR of a patient, data from a patient device, or data from a patient portal to initiate a follow-up (e.g., personal health question or encounter). Notification tools and scheduling functionality are provided via a user interface of the patient device to improve clinical workforce capacity, increase the number of patient touches, and encourage heightened patient engagement.

20 Claims, 12 Drawing Sheets

(51) Int. Cl.
*G16H 10/60* (2018.01)
*G06F 16/951* (2019.01)
*G16H 50/30* (2018.01)

(56) References Cited

U.S. PATENT DOCUMENTS

| | | | |
|---|---|---|---|
| 2015/0332012 A1* | 11/2015 | Edelson | A61B 5/7275 |
| | | | 705/2 |
| 2016/0262681 A1* | 9/2016 | Patterson | G16H 50/20 |
| 2017/0098051 A1* | 4/2017 | Balram | G16H 70/20 |

OTHER PUBLICATIONS

Tucker et al., "The Use of Early Warning Scores to Recognise and Respond to Patient Deterioration in District Nursing", British Journal of Community Nursing, vol. 23, No. 2, Feb. 2018, pp. 76-79.
Non-Final Office Action received for U.S. Appl. No. 16/236,848, dated Jun. 1, 2020, 15 pages.

* cited by examiner

Patient Dashboard

Robinson, Jane
74 yrs F  Gender Identify: F  Admin Sex: F  DOB: July 26, 1943
Initial Visit
MRN: 12345678

Determinants of Health Profile

Profile is 63% Complete  Dynamic Risk Score: 5.4 ↑

✓ Care Giver: Joe Smith   ✓ Transportation: Car   Last Acute Admission: inpatient - 7/8/18

Clinical Risks

| Category | Low | Med | High | Range | Scale |
|---|---|---|---|---|---|
| Chronic Pain | 0 | | | 0 - 10 | Mankowski Pain Scale |
| Engagement | | 4 | | 10 - 1 | Stanford Self Efficacy for Chronic Management |
| Med Adherence | | 6 | | 1 - >=8 | Morisky 8 - MMAS-8 |
| SOB | | | 4 | 1 - 4 | MMRC Dyspnea Scale |
| Fall Risk | | | 8 | 0 - 10 | MAHC-10 |
| Depression | 1 | | | 0 - >=3 | PHQ-2 |
| Anxiety | | 4 | | 0 - >=15 | GAD-7 |
| BMI | 19.5 | | | 18.5 - >=30 | -- |
| Confusion | 0 | | | 0 - 10 | CAM Tool |

Determinants of Health

| Category | Detail |
|---|---|
| ▼ SDOH and Devices | |
| Social | |
| Environmental | Spouse: Jim Robinson   Dixie |
| Assistive | |
| Trackers | |
| ▶ Precautions | |

Show Less ▲

Recent Touchpoints

Reason for Community Care
7/8/18 - Jane had a fall at home that resulted in a 4 day hospital stay with admitting diagnosis of R shoulder

Visit Tasks

0 of 5 tasks completed

✓ Complete Start of Care Assessment

FIG. 4

Patient Dashboard

Robinson, Jane
74 yrs F  Gender Identify: F  Admin Sex: F  DOB: July 26, 1943
Initial Visit
MRN: 12345678

Determinants of Health Profile

Profile is 63% Complete  Dynamic Risk Score: 6.4 ↑

Show More ▾

Recent Touchpoints

Reason for Community Care
7/8/18 - Jane had a fall at home that resulted in a 4 day hospital stay with admitting diagnosis of R shoulder dislocation, R knee laceration requiring sutures, and bruised ribs. She was discharged home with a Community Care referral.

Transitions of Care Document

7/13/18 - HealtheLife Tasks
Completed PHQ-2 and MMRC

7/12/18 - PT Visit
C/O soreness and fatigue. Intervention: PT assessment, HEP established, pain management.

7/11/18 - ITC triggered RN Video Visit
F/U on Wound and Weight Gain. Wound drainage decreased and weight down 4 pounds after scheduled Lasix.

7/10/18 - RN Visit
C/O Soreness, R Knee lac. Drainage, 2 lb weight gain in past 24hrs. Intervention: R knee dressing changed. Instructed/educated on deep breathing for pneumonia prevention, Tylenol use and Fluid Restriction/Low Na Diet

Visit Tasks 0 of 5 tasks completed

- ◯ Complete Start of Care Assessment
- ◯ Home Environment Assessment
- ◯ SDOH Profile (3)
- ◯ HealtheLife App Coaching
- ◯ HealtheRegistries (4)

Active Medications

Coumadin (warfarin sodium) ⚠
2 mg po daily. Check INR weekly. Goal range INR 2.5-3.5   pm

Lantus (insulin glargine) ⚠
16 Units subcutaneous daily at bedtime

Xanax (alprazolam) ⚠
0.5mg po q 8 hrs PRN anxiety

Tylenol (acetaminophen)   pm
500 mg 1-2 tabs po q 12 hours pm pain.

Claritin (loratadine)

Conditions and Active Diagnoses

E11.65 Type 2 Diabetes Mellitus with Hyperglycemia

E78.00 Pure Hypercholesterolemia, unspecified

F41.1 Generalized Anxiety Disorder

I10 Essential Primary Hypertension

I48.91 Unspecified Atrial Fibrillation

I50.9 Heart Failure, unspecified

S20.219A Contusion of unspecified front wall of thorax, initial encounter

FIG. 5

Tasks and Assessments

Robinson, Jane — Initial Visit
74 yrs F  Gender Identify: F  Admin Sex: F  DOB: July 26, 1943    MRN: 12345678

Assessment Results and Suggestions

Dynamic Risk Score

7.5 up from 5.4

Key Risk Indicators

| Concern | Reason |
|---|---|
| Last Hospital Discharge | <10 days |
| Poly Pharmacy | 9 |
| Poly Chronic Conditions | 5 |
| HbA1c | 8.5 |
| Anxiety | 12 |

| Name | 7/16 | 7/15 | 7/14 |
|---|---|---|---|
| Measurement | | | |
| Systolic BP | 152 | 141 | 135 |
| Diastolic BP | 91 | 84 | 79 |
| Heart Rate | 110 | 82 | 84 |
| Temperature | 101.5 | 100.9 | 99.1 |
| Weight | 135 | 134 | 132 |
| Steps | 1900 | 2200 | 2600 |
| Symptoms | | | |
| Lower Extremity Edema | X | | |
| Shoulder Pain | X | X | X |
| Shortness of Breath | X | | |
| Wound Redness/Drainage | X | X | |
| Weakness/Lethargy | X | X | X |

3 Plan Suggestions

Clean wound and change dressing daily and as needed.
1. Wash your hands with soap and water.
2. Clean wound with soap and water. You may do this in the shower. No baths/soaking/swimming until sutures are removed.
3. Dry wound with clean gauze.
4. Apply triple antibiotic ointment with cotton swab.
5. Cover with clean gauze and secure with tape.

☑ Add to Plan

Monitor weight daily.
1. Take diuretic as prescribed
2. Maintain low sodium diet
3. Increase mobility ☑ Add to Plan

RN Video Visit FU in 24 hours to assess wound and weight gain.

⦿ Accept and schedule
○ Reject

☑ Schedule

Skip    Save

FIG. 6

DYNAMICALLY UPDATING A COMMUNITY EARLY WARNING SCORE

CROSS-REFERENCE

This application claims priority to U.S. Provisional Patent Application No. 62/742,754, filed on Oct. 8, 2018, which is hereby incorporated by reference in its entirety.

BACKGROUND

Early warning systems are often used in the clinical setting (e.g., acute care) to detect patient deterioration and drive clinical decision-making. For example, the early warning system may detect that a particular condition a patient has been diagnosed with or a particular medication the patient is being treated with makes the patient a higher risk for a particular negative outcome. Unfortunately, these systems are limited to the clinical setting and do not account for, for example, a patient in a community care setting (e.g., in person visit in the community, in person visit at a clinic, clinical video visit, telephonic assessment or follow-up, electronic assessment via a patient portal or a voice system, upstream transition to a higher level of care setting, or a referral for an outside service such as transportation, meal service, or behavioral health evaluation). Moreover, these systems fail to consider additional patient information that is particularly relevant outside of a clinical facility (e.g., social determinant of health risk factors such as transportation limitations or food insecurity). This results in overlooked risk factors for the patient that increases the risk of deterioration or an acute event, resulting in an overall increase in health care costs.

Various touch points may be needed based on the needs of a particular patient in a community care setting. For example, based on demographics corresponding to the patient, a particular condition the patient has been diagnosed with or the particular medication the patient is being treated with, or other factors, the patient may need follow-ups at particular time intervals. However, in the community care setting, in-person follow-ups are not always needed and are over-utilized which results in inefficient workforce management and fewer patient touch points. This results in unnecessary or missed touch points, unnecessary in-person appointments, and an overall increase in health care costs.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces for providing intelligent touch care. More particularly, embodiments of the present disclosure utilizes contributing data elements in a community early warning score (CEWS) to predict touchpoint discipline and to recommend frequency, modality, and upstream transitions of care and outside service referrals for a patient in a community care setting. In response to a touch point (e.g., a change in condition or medication, a scheduled or unscheduled appointment, or a patient question), the CEWS can be utilized along with data in an EHR of a patient, data from a patient device, or data from a patient portal to initiate a follow-up (e.g., personal health question or encounter). Notification tools and scheduling functionality are provided via a user interface of the patient device to improve clinical workforce capacity, increase the number of patient touches, and encourage heightened patient engagement. Moreover, the ability to capture dynamic rising risk provides clinical insight into changing risk outside of the controlled environment of a clinical facility. Overall, outcomes for the patient can be improved, touch points can be increased, and unnecessary in-person appointments and overall health care costs can be reduced.

BRIEF DESCRIPTION OF THE SEVERAL VIEWS OF THE DRAWINGS

The patent or application file contains at least one drawing executed in color. The present invention is described in detail below with reference to the attached drawing figures, wherein:

FIG. 4 depicts an illustrative screen display of a community early warning score interface, in accordance with an embodiment of the present invention;

FIGS. 5-6 depict illustrative screen displays of an intelligent touch care interface, in accordance with an embodiment of the present invention;

DETAILED DESCRIPTION

Figure 1:
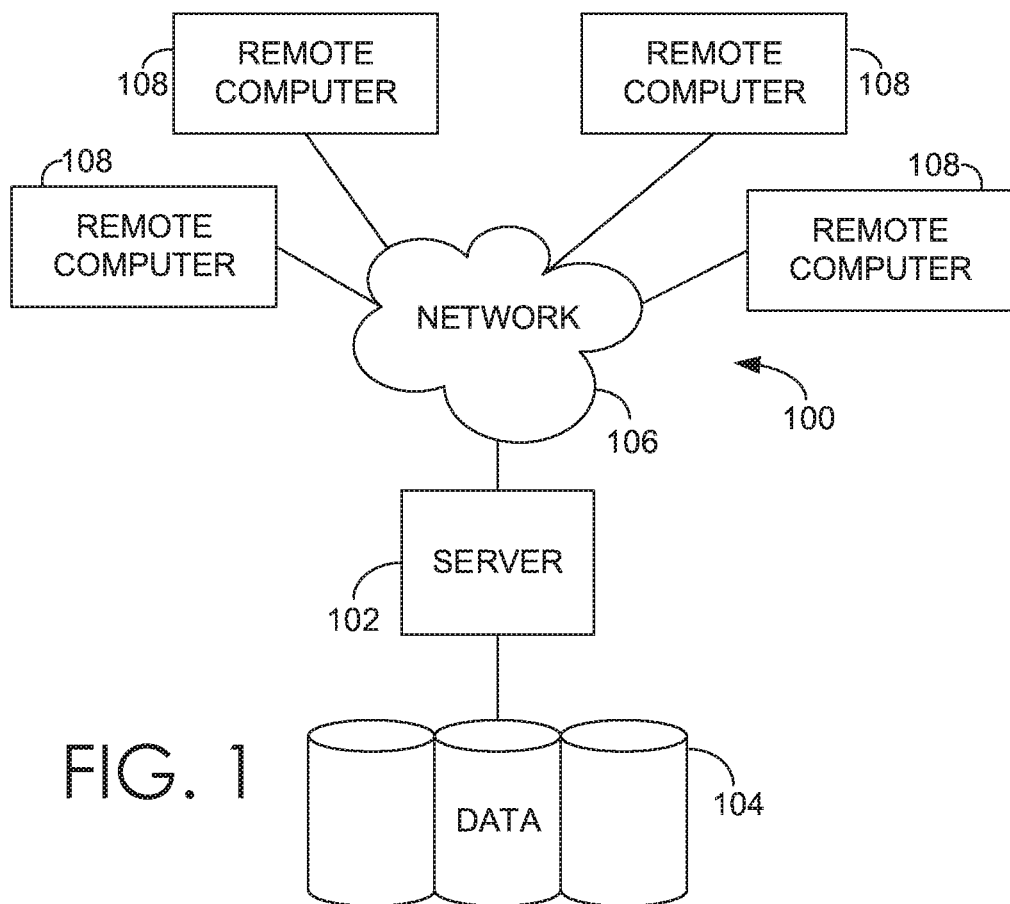
FIG. 1 is a block diagram of an exemplary operating environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the background, early warning systems are often used in the clinical setting (e.g., acute care) to detect patient deterioration and drive clinical decision-making. For example, the early warning system may detect that a particular condition a patient has been diagnosed with or a particular medication the patient is being treated with makes the patient a higher risk for a particular negative outcome. Unfortunately, these systems are limited to the clinical setting and do not account for, for example, a patient in a community care setting. Moreover, these systems fail to consider additional patient information that is particularly relevant to a patient in a community care setting. This results in overlooked risk factors for the patient that increases the risk of deterioration or an acute event, resulting in an overall increase in health care costs.

Various touch points may be needed based on the needs of a particular patient in a community care setting. For example, based on demographics corresponding to the patient, a particular condition the patient has been diagnosed with or the particular medication the patient is being treated with, or other factors, the patient may need follow-ups at particular time intervals. However, in the community care setting, in-person follow-ups are not always needed and are over-utilized which results in inefficient workforce management and fewer patient touch points. This results in unnecessary or missed touch points, unnecessary in-person appointments, and an overall increase in health care costs.

Embodiments of the present disclosure relate to systems, methods, and user interfaces for providing intelligent touch care. More particularly, embodiments of the present disclosure utilizes contributing data elements in a community early warning score (CEWS) to predict touchpoint discipline and to recommend frequency, modality, and upstream transitions of care and outside service referrals for a patient in a community care setting. In response to a touch point (e.g., a change in condition or medication, a scheduled or unscheduled appointment, or a patient question), the CEWS can be utilized along with data in an EHR of a patient, data from a patient device, or data from a patient portal to initiate a follow-up (e.g., personal health question or encounter).

Notification tools and scheduling functionality are provided via a user interface of the patient device to improve clinical workforce capacity, increase the number of patient touches, and encourage heightened patient engagement. Moreover, the ability to capture dynamic rising risk provides clinical insight into changing risk outside of the controlled environment of a clinical facility. Overall, outcomes for the patient can be improved, touch points can be increased, and unnecessary in-person appointments and overall health care costs can be reduced.

Accordingly, one embodiment of the present disclosure is directed to one or more computer storage media having computer-executable instructions embodied thereon that, when executed by a computer, causes the computer to perform operations. The operations comprise receiving a touch point for a patient in a community care setting. The touch point corresponds to a change in a condition or order. The operations also comprise, in response to the touch point, crawling data in an electronic health record (EHR) for the patient. The operations further comprise, based on the touch point and the data in the EHR, triggering a follow-up for the patient. The operations also comprise, in response to the follow-up, notifying the patient.

In another embodiment, the present disclosure directed to a computerized method. The method comprises receiving a touch point for a patient in a community care setting. The touch point corresponds to a change in a condition or order. The method also comprises, in response to the touch point, crawling data in an electronic health record (EHR) for the patient. The data includes a community early warning score (CEWS). The method further comprises, based on the touch point and the data in the EHR, triggering a follow-up for the patient. The method also comprises, in response to the follow-up, notifying the patient with a notification provided via a consumer device or personal assistant voice service, the notification indicating that a personal health question is available for the patient.

In yet another embodiment, the present disclosure is directed to a system. The system comprises a processor; and a computer storage medium storing computer-usable instructions that, when used by the processor, cause the processor to: receive a touch point for a patient in a community care setting, the touch point corresponding to a change in a condition or order; in response to the touch point, crawl data in an electronic health record (EHR) for the patient, the data including a community early warning score (CEWS); based on the touch point and the data in the EHR, trigger a follow-up for the patient; and in response to the follow-up, notify the patient with a notification provided via a consumer device or personal assistant voice service, the notification indicating that a personal health question is available for the patient.

Another of the present disclosure is directed to one or more computer storage media having computer-executable instructions embodied thereon that, when executed by a computer, causes the computer to perform operations. The operations comprise receiving a touch point for a patient in a community care setting, the touch point corresponding to a new order provided during an unscheduled appointment. The operations also comprise, in response to the touch point, communicating data corresponding to the touch point to an electronic health record (EHR) for the patient. The operations further comprise, crawling data in the EHR for the patient. The data includes a community early warning score (CEWS). The operations also comprise, based on the touch point and the data in the EHR, triggering a follow-up comprising a notification for the patient. The operations further comprise, in response to the follow-up, scheduling an encounter or generating a new touch point.

In another embodiment, the present disclosure directed to a computerized method. The method comprises receiving a touch point for a patient in a community care setting. The touch point corresponds to a new order provided during an unscheduled appointment. The method also comprises, in response to the touch point, communicating data corresponding to the touch point to an electronic health record (EHR) for the patient. The method further comprises crawling data in the EHR for the patient. The data includes a community early warning score (CEWS). The method also comprises, based on the touch point and the data in the EHR, triggering a follow-up comprising a notification for the patient. The notification is provided via a consumer device or via a personal assistant voice service and indicates that a personal health question is available for the patient. The method further comprises, in response to the follow-up, scheduling an encounter or generating a new touch point.

In yet another embodiment, the present disclosure is directed to a system. The system comprises a processor; and a computer storage medium storing computer-usable instructions that, when used by the processor, cause the processor to: receive a touch point for a patient in a community care setting, the touch point corresponding to a new order provided during an unscheduled appointment; in response to the touch point, communicate data corresponding to the touch point to an electronic health record (EHR) for the patient; crawl data in the EHR for the patient. The data includes a community early warning score (CEWS); based on the touch point and the data in the EHR, trigger a follow-up for the patient; and in response to the follow-up, schedule an encounter or generate a new touch point.

Another embodiment of the present disclosure is directed to one or more computer storage media having computer-executable instructions embodied thereon that, when executed by a computer, causes the computer to perform operations. The operations comprise receiving a touch point for a patient in a community care setting. The touch point corresponds to a new order provided during a scheduled appointment. The operations also comprise, in response to the touch point, communicating data corresponding to the touch point to an electronic health record (EHR) for the patient. The operations further comprise, crawling data in the EHR for the patient. The data includes a community early warning score (CEWS). The operations also comprise, based on the touch point and the data in the EHR, triggering a follow-up comprising a notification for the patient. The operations further comprise, in response to an indication the patient has questions or concerns, initiating a telephone clinical assessment.

In another embodiment, the present disclosure directed to a computerized method. The method comprises receiving a touch point for a patient in a community care setting. The touch point corresponds to a new order provided during a scheduled appointment. The method also comprises, in response to the touch point, communicating data corresponding to the touch point to an electronic health record (EHR) for the patient. The method further comprises crawling data in the EHR for the patient. The data includes a community early warning score (CEWS). The method also comprises, based on the touch point and the data in the EHR, triggering a follow-up comprising a notification for the patient. The method further comprises, in response to an indication the patient has questions or concerns, initiating a telephone clinical assessment.

In yet another embodiment, the present disclosure is directed to a system. The system comprises a processor; and a computer storage medium storing computer-usable instructions that, when used by the processor, cause the processor to: receive a touch point for a patient in a community care setting, the touch point corresponding to a new order provided during a scheduled appointment; in response to the touch point, communicate data corresponding to the touch point to an electronic health record (EHR) for the patient; crawl data in the EHR for the patient, the data including a community early warning score (CEWS); based on the touch point and the data in the EHR, trigger a follow-up comprising a notification for the patient, the notification is provided to the patient via a consumer device or via a personal assistant voice service and indicating that a personal health question is available for the patient; based on a response to the personal health question, receive an indication the patient has questions or concerns; in response to the indication, initiate a telephone clinical assessment; and provide a recommendation to a clinician performing the telephone clinical assessment to address the questions or concerns.

Another embodiment of the present disclosure is directed to one or more computer storage media having computer-executable instructions embodied thereon that, when executed by a computer, causes the computer to perform operations. The operations comprise receiving a touch point for a patient in a community care setting. The touch point indicates the patient has a question for a clinician. The operations also comprise, in response to the touch point, communicating data corresponding to the touch point to an electronic health record (EHR) for the patient. The operations further comprise crawling data in the EHR for the patient. The data includes a community early warning score (CEWS). The operations also comprise, based on the touch point and the data in the EHR, triggering a follow-up comprising a notification for the patient or initiating a telephone clinical assessment.

In another embodiment, the present disclosure directed to a computerized method. The method comprises receiving a touch point for a patient in a community care setting. The touch point indicates the patient has a question for a clinician. The method also comprises, in response to the touch point, communicating data corresponding to the touch point to an electronic health record (EHR) for the patient. The method further comprises crawling data in the EHR for the patient. The data includes a community early warning score (CEWS). The method also comprises, based on the touch point and the data in the EHR, triggering a follow-up comprising a notification for the patient or initiating a telephone clinical assessment.

In yet another embodiment, the present disclosure is directed to a system. The system comprises a processor; and a computer storage medium storing computer-usable instructions that, when used by the processor, cause the processor to: receive a touch point for a patient in a community care setting, the touch point indicating the patient has a question for a clinician; in response to the touch point, communicate data corresponding to the touch point to an electronic health record (EHR) for the patient; crawl data in the EHR for the patient, the data including a community early warning score (CEWS); and based on the touch point and the data in the EHR, trigger a follow-up comprising a notification for the patient or initiating a telephone clinical assessment.

Another embodiment of the present disclosure is directed to one or more computer storage media having computer-executable instructions embodied thereon that, when executed by a computer, causes the computer to perform operations. The operations comprise receiving, at a community early warning score (CEWS) engine comprising a plurality of data crawlers, a request to dynamically update a CEWS for a patient. The operations also comprise initiating a first set of the plurality of data crawlers to collect data in an electronic health record (EHR) of the patient. Each of the first set of the plurality of data crawlers is responsible for collecting a distinct type of data within the EHR. The operations further comprise initiating a second set of the plurality of data crawlers to collect data originating from a patient device corresponding to the patient. The operations also comprise utilizing the data collected by the plurality of data crawlers, dynamically updating the CEWS at the CEWS engine. The operations further comprise, based on the updated CEWS, initiating a workflow for the patient at the patient device or a clinician device.

In another embodiment, the present disclosure directed to a computerized method. The method comprises receiving, at a community early warning score (CEWS) engine comprising a plurality of data crawlers, a request to dynamically update a CEWS for a patient. The method also comprises initiating a first set of the plurality of data crawlers to collect data in an electronic health record (EHR) of the patient. Each of the first set of the plurality of data crawlers is responsible for collecting a distinct type of data within the EHR. The method further comprises utilizing the data collected by the plurality of data crawlers, dynamically updating the CEWS at the CEWS engine. The method also comprises, based on the updated CEWS, initiating a workflow for the patient at the patient device or a clinician device.

In yet another embodiment, the present disclosure is directed to a system. The system comprises a processor; and a computer storage medium storing computer-usable instructions that, when used by the processor, cause the processor to: receive, at a community early warning score (CEWS) engine comprising a plurality of data crawlers, a request to dynamically update a CEWS for a patient; initiate a first set of the plurality of data crawlers to collect data in an electronic health record (EHR) of the patient, each of the first set of the plurality of data crawlers responsible for collecting a distinct type of data within the EHR; initiate a second set of the plurality of data crawlers to collect data originating from a patient device corresponding to the patient; utilizing the data collected by the plurality of data crawlers, dynamically update the CEWS at the CEWS engine; and based on the updated CEWS, initiate a workflow for the patient at the patient device or a clinician device.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home health care environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire health care community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote health care device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
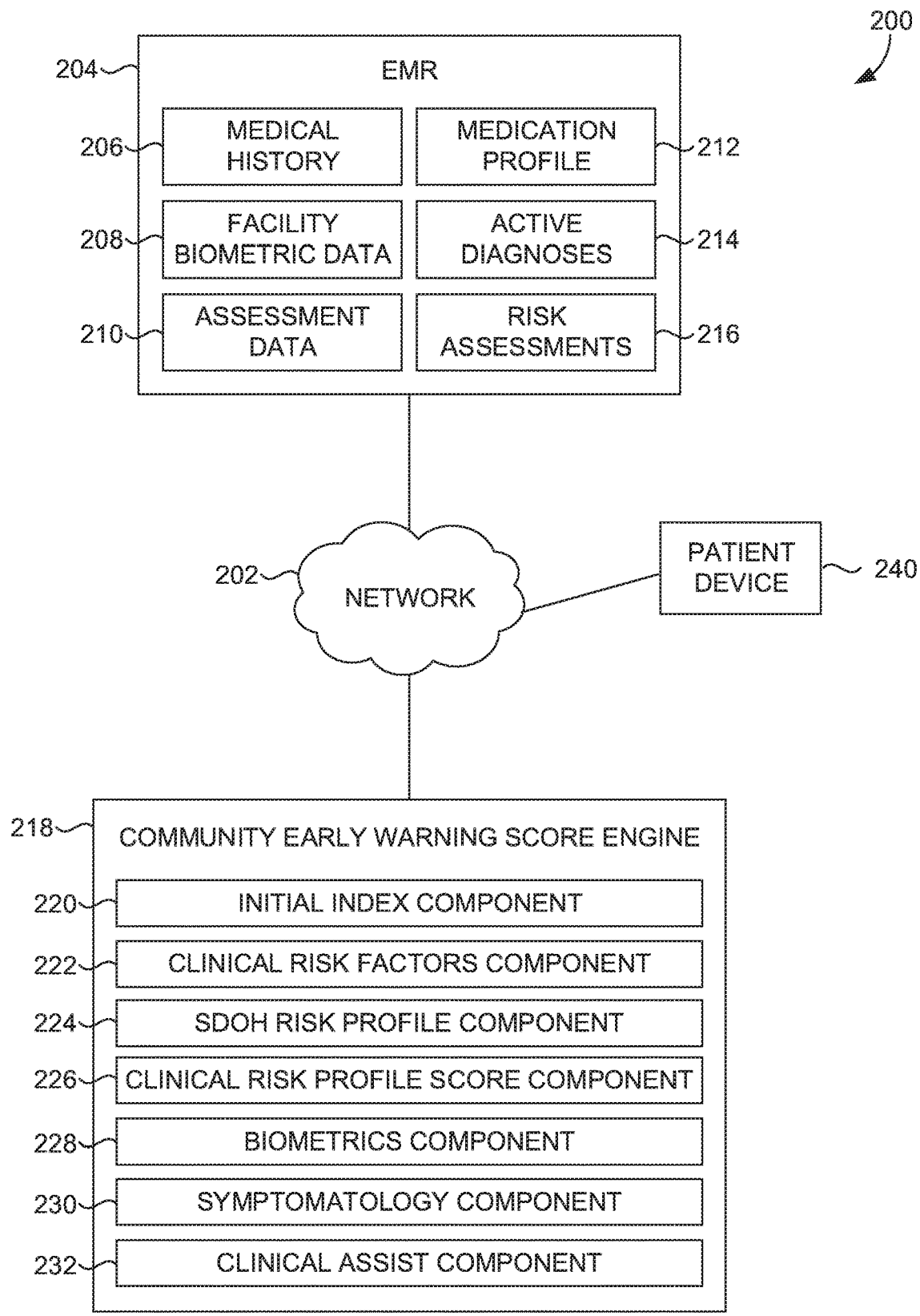
FIG. 2 depicts an exemplary framework of a community early warning score system suitable to implement embodiments of the present invention.

Turning now to FIG. 2, an exemplary framework of a community early warning score (CEWS) system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The CEWS system 200 may be implemented via any type of computing device, such as computing device 100 described above with reference to FIG. 1, for example.

The CEWS system 200 generally operates to determine a CEWS for a patient. More particularly, the CEWS system 200 dynamically updates the CEWS for the patient which may be utilized by an intelligent touch care system to provide a workflow to a patient device 240 and/or a clinician device (e.g., clinician device 316 of FIG. 3). To do so, the CEWS system utilizes the data in an EHR to periodically dynamically update the CEWS of the patient which can be utilized by an intelligent touch care engine (such as the intelligent touch care engine 306 of FIG. 3), as described herein, to improve outcomes for the patient, increase overall touch points, reduce unnecessary in-person appointments, and reduce overall health care costs. In some embodiments, an update to the CEWS may trigger a workflow provided by the intelligent touch care engine.

As shown in FIG. 2, the CEWS system 200 includes, among other components not shown, EHR 204, CEWS engine 218, and patient device 240. It should be understood that the CEWS system 200 shown in FIG. 2 is an example of one suitable computing system architecture. Each of the components shown in FIG. 2 may be implemented via any type of computing device, such as computing device 100 described with reference to FIG. 1, for example.

The components may communicate with each other via a network 202, which may include, without limitation, one or more local area networks (LANs) and/or wide area networks (WANs). Such networking environments are commonplace in offices, enterprise-wide computer networks, intranets, and the Internet. It should be understood that any number of EHRs and CEWS engines may be employed within the CEWS system 200 within the scope of the present disclosure. Each may comprise a single device or multiple devices cooperating in a distributed environment. For instance, the CEWS engine 218 (or any of its components: initial index component 220, clinical risk factors component 222, social determinants of health (SDOH) risk profile component 224, clinical risk profile score component 226, biometrics component 228, symptomatology component 230, and clinical assist component 232) and/or the EHR 204 may be provided via multiple devices arranged in a distributed environment that collectively provide the functionality described herein. In other embodiments, a single device may provide the functionality of multiple components of the CEWS system 200. For example, a single device may provide the EHR 204 and the CEWS engine 218. In some embodiments, some or all functionality provided by the CEWS engine 218 (or any of its components) may be provided by a patient device or a clinician device (such as patient device 240 or clinician device 316 of FIG. 3). Additionally, other components not shown may also be included within the network environment.

EHR 204 includes an electronic version of patient records including information for the patient, such as surveys, trauma documentation, including images, clinical notes, orders, summaries, reports, analyses, information received from medical devices, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information. The content and volume of such information in the EHR is not intended to limit the scope of embodiments of the present invention in any way.

As shown, EHR 204 includes medical history 206, facility biometric data 208, assessment data 210, medication profile 212, active diagnoses 214, and risk assessments 216. The data that comprises each of these components of EHR 204 can be utilized by various components of the CEWS engine 218 at various time intervals to dynamically update a CEWS. The CEWS combines the National Early Warning Score 2, a comprehensive risk profile, clinical assessment data and biometric data to predict rising risk of: 1) a condition or chronic disease exacerbation; 2) a clinical system decline; or 3) an acute event or change (e.g., urinary tract infection or pneumonia). Although the CEWS is described herein with reference to a community care setting, it is contemplated that the CEWS is venue agnostic and can be utilized across any post-acute or acute venues.

Generally, and as mentioned, the CEWS engine 218 crawls data in the EHR to dynamically update the CEWS. As shown, the CEWS engine 218 comprises an initial index component 220, a clinical risk factors component 222, a social determinants of health (SDOH) risk profile component 224, a clinical risk profile score component 226, a biometrics component 228, symptomatology component 230, and a clinical assist component 232. Each of the components of CEWS engine 218 are responsible for crawling a distinct type of data within the EHR 204.

For example, initial index component 220 crawls facility biometric data 208 and assessment data 210 of EHR 204 to calculate the National Early Warning Score 2 for a patient. The assessment data includes respiratory rate, an estimate of arterial oxygen saturation, hypercapnia, supplemental Oxygen, systolic blood pressure, heart rate, level of consciousness (or new onset confusion), temperature, and the like.

Clinical risk factors component 222 crawls medical history 206 and medication profile 212 of EHR 204 to determine the clinical risk factors of the patient. The clinical risk factors may include if the patient is an opioid risk, an amputee, body mass index, utilizes a medicinal sleep aid, is paraplegic or quadriplegic, has a recent acute admission, is polychronic or polypharmacy, and the like.

Social determinants of health (SDOH) risk profile component 224 crawls assessment data 210 and risk assessments 216 of EHR 204 to determine a SDOH risk profile of the patient. The SDOH risk profile may include various factors corresponding to the patient such as the current housing situation of the patient, transportation available to the patient, utilities available to the patient, a financial situation of the patient, a health literacy of the patient, modes of communication available to the patient, social engagement of the patient, stress of the patient, food insecurity of the patient, and the like.

Clinical risk profile score component 226 crawls risk assessments 216 of EHR 204 to determine a clinical risk profile score. The clinical risk profile score may be comprised of risks corresponding to pain, fall, depression, anxiety, dyspnea, Activities of Daily Living/Instrumental Activities of Daily Living, frail or elderly, medication adherence, engagement, confusion, suicide risk, post-traumatic stress disorder, and the like.

Biometrics component 228 crawls facility biometric data 208 and assessment data 210 of EHR 204 to determine biometrics for the patient. Biometrics may include temperature, heart rate, systolic blood pressure, diastolic blood pressure, mean arterial blood pressure, weight, glucose, supplemental Oxygen, an estimate of arterial oxygen saturation, respiratory rate, activity, sleep, and the like.

Symptomatology component 230 crawls assessments 216 of EHR 204 to determine symptomology for the patient. Symptomatology may include any assessed symptoms.

Clinical assist component 232 crawls facility biometric data 208 of EHR 204 to determine clinical assist mechanisms associated with the patient. For example, clinical assist mechanisms may include whether the patient is on oxygen, infusion, a particular nutrition plan, dialysis, chemotherapy, radiation, assistive devices, and the like.

Additional information from patient device 240 may be crawled by clinical risk factors component 222, social determinants of health (SDOH) risk profile component 224, clinical risk profile score component 226, biometrics component 228, symptomatology component 230, and clinical assist component 232. Additionally or alternatively, the information from patient device 240 may be initially communicated from patient device 240 to EHR 204 where it is stored and later crawled by one of clinical risk factors component 222, social determinants of health (SDOH) risk profile component 224, clinical risk profile score component 226, biometrics component 228, symptomatology component 230, and clinical assist component 232.

The additional information may be derived from a symptom diary of the patient, biometric data from a device owned or utilized by the patient, biometric data from a prescribed kit, caregiver risk assessments (i.e., community home health caregiver), patient schedule, personal data of the patient, and the like.

CEWS engine 218 utilizes the data crawled by each of the components of CEWS engine 218 to periodically dynamically update the CEWS of the patient which can be utilized by an intelligent touch care engine (such as the intelligent touch care engine 306 of FIG. 3), as described herein, to improve outcomes for the patient, increase overall touch points, reduce unnecessary in-person appointments, and reduce overall health care costs. In some embodiments, an update of the CEWS communicated by the CEWS engine 218 to the intelligent touch care engine may trigger a workflow provided by the intelligent touch care engine.

Figure 3:
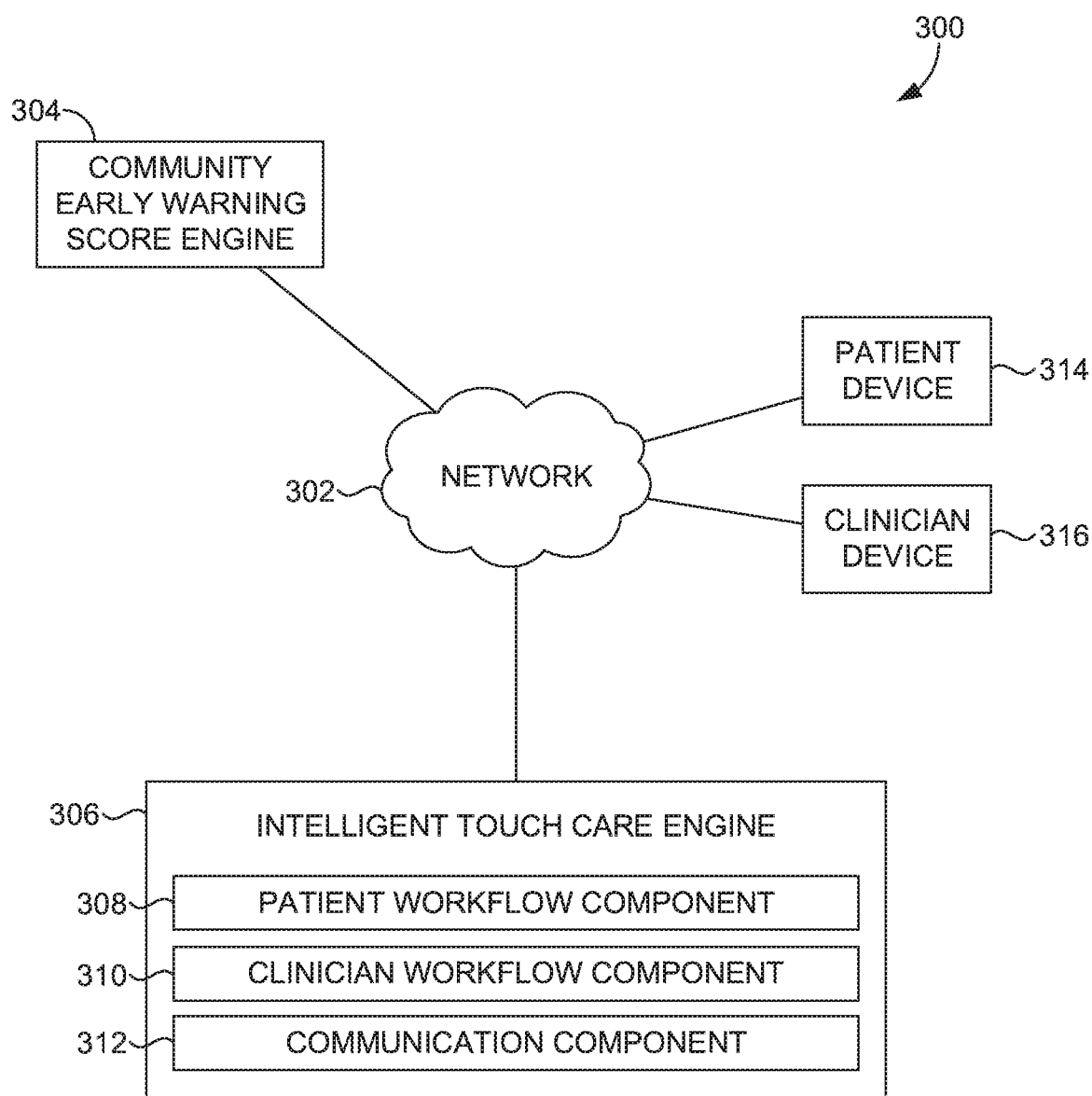
FIG. 3 depicts an exemplary framework of an intelligent touch care system suitable to implement embodiments of the present invention.

Referring now to FIG. 3, an exemplary framework of an intelligent touch care system 300 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The intelligent touch care system 300 may be implemented via any type of computing device, such as computing device 100 described above with reference to FIG. 1, for example.

The intelligent touch care system 300 generally operates to provide intelligent touch care for a patient. More particularly, the intelligent touch care system 300 utilizes contributing data elements in the CEWS to predict touchpoint discipline and to recommend frequency, modality, and upstream transitions of care and outside service referrals. As described above, the CEWS is a dynamic risk score used for risk stratification for a patient in a community care setting. In response to a touch point (e.g., a change in condition or medication, a scheduled or unscheduled appointment, or a patient question), the CEWS can be utilized along with data in an EHR of a patient, data from a patient device, or data from a patient portal to initiate a follow-up (e.g., personal health question or encounter).

As shown in FIG. 3, the intelligent touch care system 300 includes, among other components not shown, community early warning score (CEWS) engine 304, intelligent touch care engine 306, patient device 314, and clinician device 316. It should be understood that the intelligent touch care system 300 shown in FIG. 3 is an example of one suitable computing system architecture. Each of the components shown in FIG. 3 may be implemented via any type of computing device, such as computing device 100 described with reference to FIG. 1, for example.

The components may communicate with each other via a network 302, which may include, without limitation, one or more local area networks (LANs) and/or wide area networks (WANs). Such networking environments are commonplace in offices, enterprise-wide computer networks, intranets, and the Internet. It should be understood that any number of hinting engines and vocabulary databases may be employed within the intelligent touch care system 300 within the scope of the present disclosure. Each may comprise a single device or multiple devices cooperating in a distributed environment. For instance, the intelligent touch care engine 306 (or any of its components: patient workflow component 308, clinician workflow component, and communication component 312) and/or the CEWS engine 304 may be provided via multiple devices arranged in a distributed environment that collectively provide the functionality described herein. In other embodiments, a single device may provide the functionality of multiple components of the intelligent touch care engine 306. For example, a single device may provide the intelligent touch care engine 306 and/or the CEWS engine 304. In some embodiments, some or all functionality provided by the intelligent touch care engine 306 (or any of its components) and/or the CEWS engine 304 may be provided by a patient device 314 or a clinician device 316. Additionally, other components not shown may also be included within the network environment.

Generally, the intelligent touch care engine 306 provides intelligent touch care for a patient. The intelligent touch care engine 306 provides notification tools and scheduling functionality via a user interface of the patient device 314 to improve clinical workforce capacity, increase the number of patient touches, and encourage heightened patient engagement. Moreover, the ability to capture dynamic rising risk provides clinical insight into changing risk outside of the controlled environment of a clinical facility. Overall, outcomes for the patient can be improved, touch points can be increased, and unnecessary in-person appointments and overall health care costs can be reduced.

As described above, the intelligent touch care engine 306 includes several components including a patient workflow component 308, a clinician workflow component 310, and a communication component 312. The patient workflow component 306 generally provides the notification tools and scheduling functionality described herein for the patient via a user interface of the patient device 314. The patient workflow component 306 enables the patient to interact with a clinician, such as via telephone clinical assessments or video visits, or to enable the patient to ask questions of or express concerns to the clinician. In embodiments, the patient device 314 may include a personal assistant voice service (e.g., ALEXA). Additionally, the patient workflow component 306 may guide the patient through a series of tasks or self-assessments that may be part of the overall workflow initiated by a touch point and/or utilized by CEWS engine 304 to dynamically update the CEWS of the patient.

The clinician workflow component 310 generally provides notification tools and scheduling functionality for a clinician via a user interface of the clinician device 316. The clinician workflow component 310 enables the clinician to interact with the patient, such as via telephone clinical assessments or video visits, or to enable the clinician to receive and/or answer concerns expressed by or questions asked by the patient. Additionally, the clinician workflow component 310 may guide the clinician through a series of tasks, assessments, and/or clinical decision support that may be part of the overall workflow initiated by a touch point.

The communication component 312 generally communicates and/or receives data utilized by the intelligent touch care engine 306. For example, the communication component 312 may receive updates to the CEWS from the CEWS engine 304. Additionally, the communication component may provide data to the CEWS engine 304 received from other components of the intelligent touch care engine 306 to dynamically update the CEWS. The communication component 312 may also receive data from the patient device 314 and/or the clinician device 316 that may be utilized to provide features of other components of the intelligent touch care engine 306.

With reference to FIGS. 4-6, illustrative screen displays 400, 500, 600 of embodiments of the present invention are shown. It is understood that each of the illustrative screen displays are connected logically, such that they comprise a user interface designed for an intelligent touch care system, in accordance with embodiments of the present invention. The screen displays may appear in any order and with any number of screen displays, without regard to whether the screen display is described or depicted herein. The screen displays provide tools that enable more frequent, more effective, and more efficient care in a community care setting, in accordance with embodiments of the present invention.

In FIG. 4, an illustrative screen display of a CEWS interface 400 is shown, in accordance with an embodiment of the present invention. As illustrated, the CEWS interface 400 enables a patient to complete the patient profile that includes clinical risks and determinants of health. The information provided by the patient to the CEWS interface 400 is a portion of the data utilized by a CEWS engine (such as CEWS engine 218, 304 of FIGS. 2 and 3) to determine a dynamically updated CEWS for the patient.

Turning to FIGS. 5-6, illustrative screen displays of an intelligent touch care interface 500, 600 are shown, in accordance with an embodiment of the present invention. In FIG. 5, recent touchpoints and visit tasks are provide to the patient. Each of the recent touchpoints and visit tasks may include various documents, assessments, and/or other information that may require additional action by the patient. As a result of the additional action, the CEWS may be updated by a CEWS engine (such as CEWS engine 218, 304 of FIGS. 2 and 3) which may update a workflow provided by an intelligent touch care engine (such as the intelligent touch care engine 306 of FIG. 3). In FIG. 6, the visit tasks has been expanded to show an updated CEWS, key risk indicators, and plan suggestions (which may include an ability to schedule a follow-up with a clinician as part of the workflow).

Figure 7:
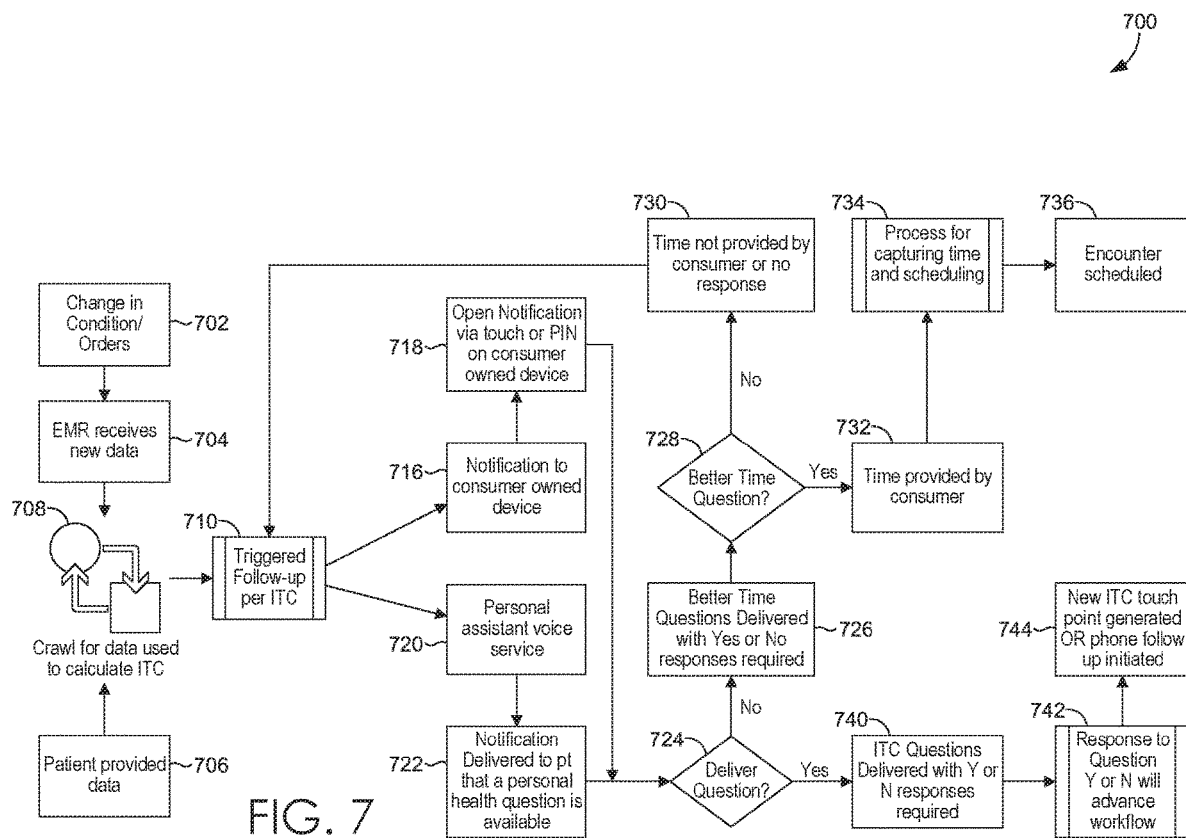
FIG. 7 depicts a flow diagram of a method illustrating a touch point corresponding to a change in a condition or an order that initiates a workflow, in accordance with an embodiment of the present invention.

In FIG. 7, a flow diagram of a method illustrating a touch point corresponding to a change in a condition or an order that initiates a workflow is depicted, in accordance with an embodiment of the present invention. Method 700 may be performed by any computing device (such as computing device described with respect to FIG. 1) with access to a CEWS system and/or an intelligent touch care system (such as the systems described with respect to FIGS. 2 and 3) or by one or more components of the CEWS system and/or intelligent touch care system.

Initially, as shown at step 702, a touch point corresponding to a change in a condition or order is received for a patient in a community care setting. At step 704, the EHR receives new data corresponding to the touch point. Data may also be provided by patient, at step 706, and stored in EHR. In response to the touch point being received, data is crawled in the EHR for the patient, at step 708, to determine the appropriate workflow for the patient. Additionally, data provided by the patient may also be crawled.

At step 710, based on the touch point and the CEWS, a follow-up is triggered for the patient. In response to the follow-up, the patient is notified at step 716 and/or step 720. For example, the notification may be provided via a consumer device, as shown at step 716. The user may open the notification, at step 718, via touch or password on the consumer device. Additionally, or alternatively, the notification may be provided via a personal assistant voice service, as shown at step 720. The notification may indicate, at step 722, that a personal health question is available for the patient.

At step 724, it is determined if the personal health question has been delivered to the patient. If the personal health question has not been delivered to the patient, as shown at step 726, the patient may be the patient is prompted, at step 728, to provide a time the patient is available to answer the personal health question. In response to the patient providing a time the patient is available to answer the personal health question, at step 732, the time is captured and an encounter is scheduled, at step 736, for the patient. Alternatively, as shown at step 730, in response to the patient not providing a time the patient is available to answer the personal health question, a second follow-up is triggered, as shown at step 710, for the patient.

If an indication that the patient is available to answer the personal health question is received, as shown at step 740, the intelligent touch care questions are delivered to the patient. If the patient provides a response tot eh intelligent touch care questions, as shown at step 742, the intelligent touch care workflow is advanced. Consequently, a second touch point is generated or a telephone follow-up is initiated, at step 744.

Figure 8:
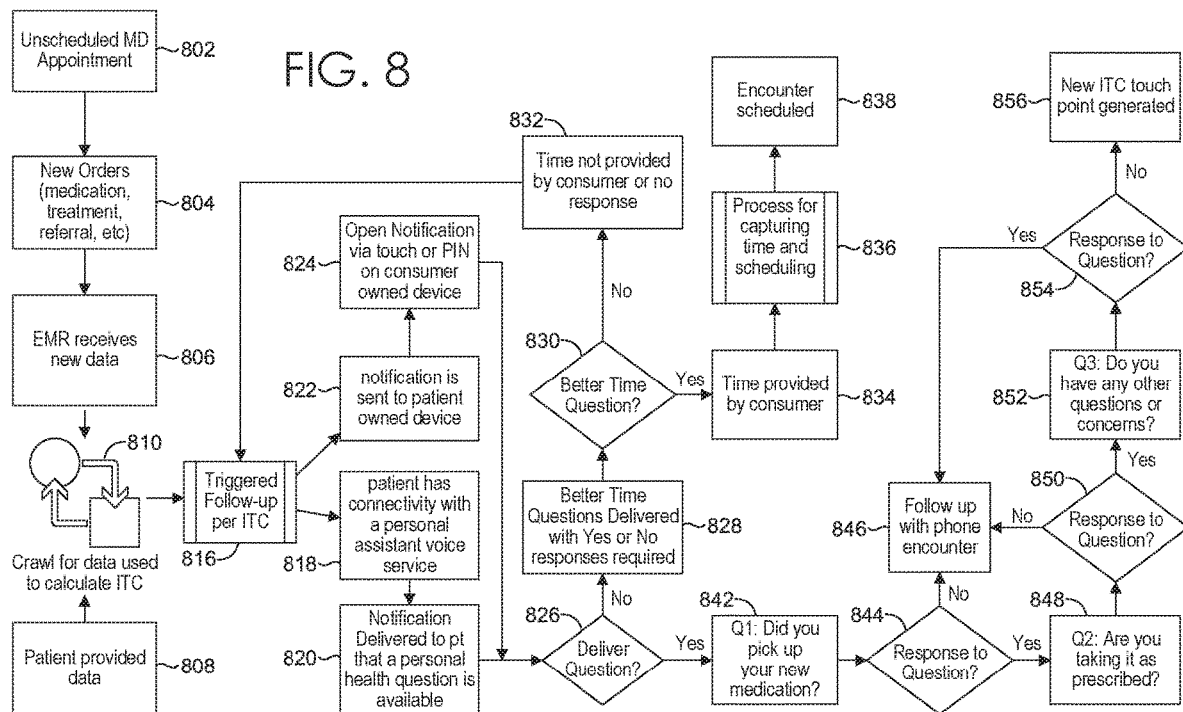
FIG. 8 depicts a flow diagram of a method illustrating a touch point corresponding to an unscheduled appointment with a clinician that initiates a workflow, in accordance with an embodiment of the present invention.

Referring FIG. 8, an exemplary flow diagram 800 illustrates a touch point corresponding to an unscheduled appointment with a clinician that initiates a workflow, in accordance with an embodiment of the present invention. Method 800 may be performed by any computing device (such as computing device described with respect to FIG. 1) with access to a CEWS system and/or an intelligent touch care system (such as the systems described with respect to FIGS. 2 and 3) or by one or more components of the CEWS system and/or intelligent touch care system.

Initially, as shown at step 802, a touch point is received for a patient in a community care setting. The touch point corresponding to a new order provided during an unscheduled appointment. In response to the touch point, data corresponding to the touch point is communicated, at step 804, to an EHR for the patient. Data is crawled, at step 806, in the EHR for the patient. The data may include a CEWS that is determined, at least in part, by patient provided data, as shown at step 808. The patient provided data be communicated to the EHR before the EHR is crawled, or may be crawled in addition to data being crawled in the EHR.

Based on the touch point and the data in the EHR (including the CEWS), a follow-up comprising a notification is triggered, at step 816, for the patient. In response to the follow-up, an encounter is scheduled or a new touch point is generated, as shown at steps 838 or 856.

In some embodiments, the notification is provided to the patient via a consumer device, as shown at step 822. The notification may be opened via touch or password on the consumer device, as shown at step 824. If the patient has connectivity with a personal assistant voice service, as shown at step 818, the notification may instead be delivered via the personal assistant voice service indicating, at step 820, that a personal health question is available for the patient.

At step 826, it is determined whether the personal health question has been communicated to the patient. Upon determining, in one embodiment as shown at step 828, the personal health question has not been communicated to the patient, the patient is prompted, at step 830, with an option to receive the personal health question at another time. Upon receiving an indication the patient has not provided another time, at step 832, a second follow-up is triggered for the patient, at step 816. Upon receiving an indication, in one embodiment as shown at step 834, the patient has provided another time, the time is captured, at step 836, to schedule the encounter, at 838.

Upon determining, in one embodiment as shown at step 826, the personal health question has been communicated to the patient, the patient is prompted, at step 842, to indicate whether the patient has complied with the new order (e.g., has the patient picked up a new medication). Upon determining, in one embodiment as shown at step 844, the patient has not complied with the new order, a telephone follow-up is initiated, at step 846, for the patient.

In some embodiments, a second question (e.g., is the patient taking the new medication as prescribed) may be communicated to the patient, as shown at step 848. If a second question is communicated and the patient does not respond, a telephone follow-up is initiated, at step 846, for the patient. Upon determining, the patient has answered all questions and/or complied with the new order, the patient is prompted, at step 852, to indicate if the patient has questions or concerns. If the patient has questions or concerns, as shown at step 854, a telephone follow-up is initiated, at step 846, for the patient. If the patient does not have questions or concerns, as shown at step 854, the second touch point is generated at step 856.

Figure 9:
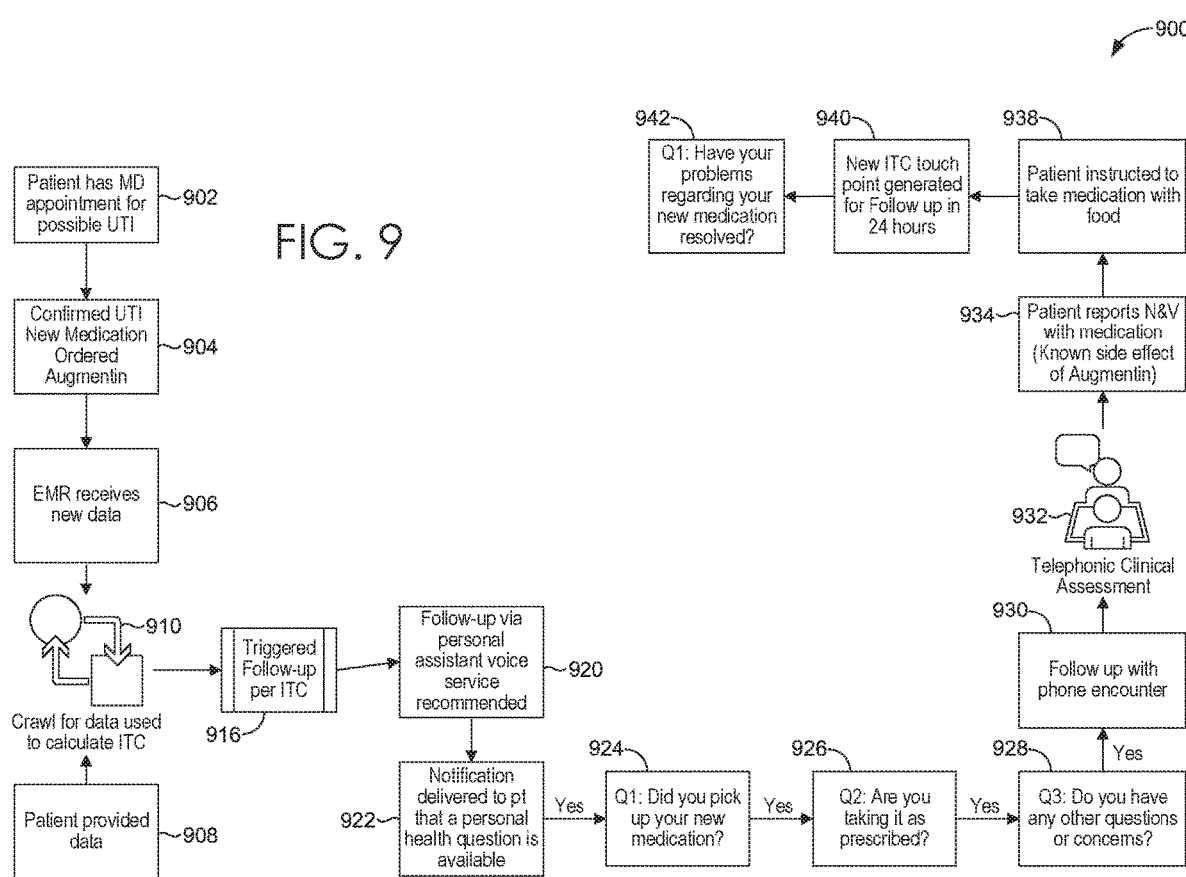
FIG. 9 depicts a flow diagram of a method illustrating a touch point corresponding to a scheduled appointment with a clinician that initiates a workflow, in accordance with an embodiment of the present invention.

Referring now to FIG. 9, an exemplary flow diagram 900 illustrates a touch point corresponding to a scheduled appointment with a clinician that initiates a workflow, in accordance with an embodiment of the present invention. Method 900 may be performed by any computing device (such as computing device described with respect to FIG. 1) with access to a CEWS system and/or an intelligent touch care system (such as the systems described with respect to FIGS. 2 and 3) or by one or more components of the CEWS system and/or intelligent touch care system.

Initially, as shown at step 902, a touch point is received for a patient in a community care setting. The touch point corresponds to a new order provided, as shown at step 904, during a scheduled appointment. In response to the touch point, data corresponding to the touch point is communicated, at step 906, to an EHR for the patient. At step 910, data is crawled in the EHR for the patient. The data may include a CEWS that is determined, at least in part, by patient provided data, as shown at step 908. The patient provided data may be communicated to the EHR before the EHR is crawled, or may be crawled in addition to data being crawled in the EHR.

Based on the touch point and the data in the EHR, a follow-up is triggered, at step 916. The follow-up may comprise a notification for the patient. The follow-up may be communicated, at step 920, to the patient via a consumer device or via a personal assistant voice service. The notification indicates, at step 922, that a personal health question is available for the patient. The personal health question may be a series of questions 924, 926, 928 (e.g., did you pick up your medication, are you taking it as prescribed, do you have any other questions or concerns, etc.).

In embodiments, as shown at step 930, upon receiving an indication the patient has questions or concerns, a follow-up may be necessary. Accordingly, a telephonic clinical assessment may be initiated at step 932. During the telephonic clinical assessment, the patient may report, at step 934, the questions or concerns. Upon receiving the questions or concerns (i.e., entry by clinician or patient, or by voice recognition), the intelligent touch care system (such as the intelligent touch care system 200 of FIG. 2), identifies the questions or concerns. As a result, the intelligent touch care system may provide, at step 938, a recommendation to a clinician performing the telephone clinical assessment the patient to address the questions or concerns. A second touch point is generated, at step 940. The second touch point triggers a second follow-up comprising a second notification for the patient that is provided to the patient via the consumer device or via the personal assistant voice service at a particular time and indicates that a second personal health question is available for the patient. For example, the second personal health question may confirm that any questions or concerns of the patient have been resolved, as shown at step 942.

Figure 10:
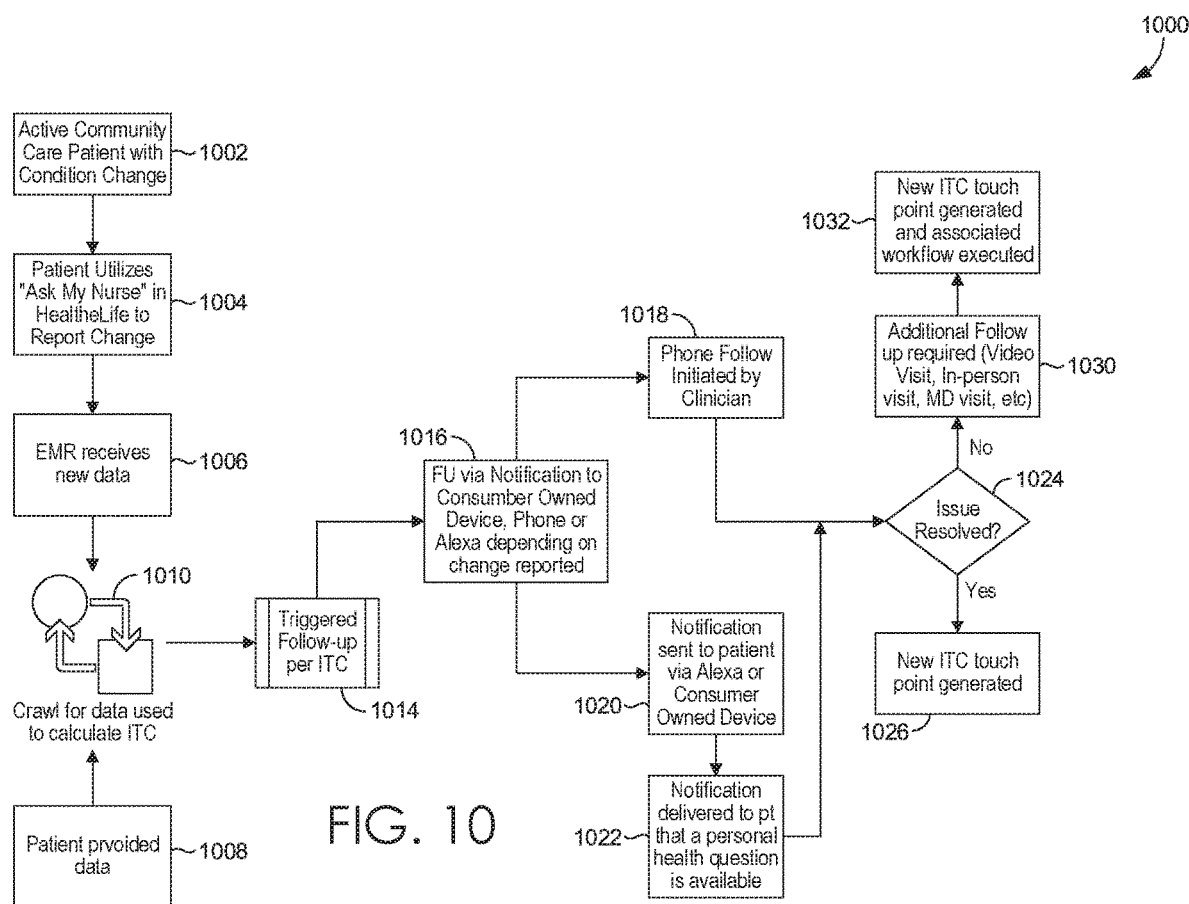
FIG. 10 depicts a flow diagram of a method illustrating a touch point corresponding to change in condition for an active community care patient that initiates a workflow, in accordance with an embodiment of the present invention.

In FIG. 10, an exemplary flow diagram 1000 illustrates a touch point corresponding to change in condition for an active community care patient that initiates a workflow, in accordance with an embodiment of the present invention. Method 1000 may be performed by any computing device (such as computing device described with respect to FIG. 1) with access to a CEWS system and/or an intelligent touch care system (such as the systems described with respect to FIGS. 2 and 3) or by one or more components of the CEWS system and/or intelligent touch care system.

Initially, as shown at step 1002, an active community care patient (i.e., a patient that interacts with an intelligent touch care system has change in a condition, as shown at step 10002. A touch point for the patient in community care is received, at step 1004. The touch point indicates the patient has a question for a clinician. In response to the touch point, data corresponding to the touch point is communicated, at step 1006, to an EHR for the patient. Data is crawled, at step 1010, in the EHR for the patient. The data may include a CEWS that is determined, at least in part, by patient provided data, as shown at step 1008. The patient provided data may be communicated to the EHR before the EHR is crawled, or may be crawled in addition to data being crawled in the EHR.

Based on the touch point and the data in the EHR, a follow-up is triggered, at step 1014. The follow-up may comprise a notification for the patient or initiating a telephone clinical assessment, as shown at step 1016. In one example, a notification is provided, at step 1020, to the patient via a personal assistant voice service. The notification may indicate, as shown at step 1022, that a personal health question is available for the patient. In another example, a telephonic follow-up may be initiated, at step 1018, to the patient via the consumer device.

At step 1024, it is determined whether the issue corresponding to the question has been resolved. Upon determining, the issue corresponding to the question has been resolved, a second touch point is generated, at step 1026, for the patient. The second touch point may indicate the issue corresponding to the question has been resolved and be communicated to the EHR.

Alternatively, upon determining the issue corresponding to the question has not been resolved, as shown at step 1030, a second follow-up is recommended. The second follow-up may comprise a video visit, an in-person visit, or a clinician visit. A second touch point is generated, at step 1032, for the patient. The second touch point may schedule the second follow-up for the patient and initiate any corresponding workflow.

Figure 11:
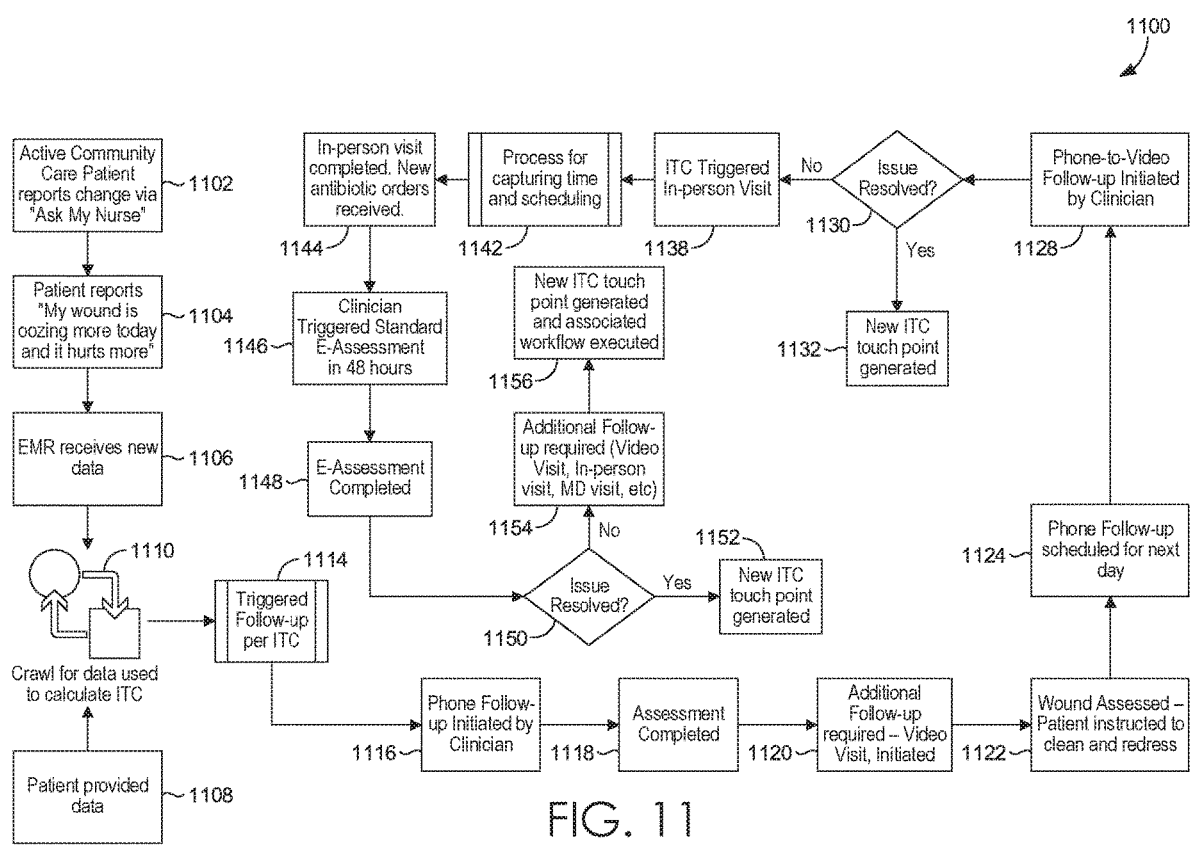
FIG. 11 is a flow diagram of a method illustrating a touch point corresponding to a patient message of an active community care patient that initiates a workflow, in accordance with embodiments of the invention.

Turning now to FIG. 11, an exemplary flow diagram illustrates a touch point corresponding to a patient message of an active community care patient that initiates a workflow, in accordance with embodiments of the invention. Method 1100 may be performed by any computing device (such as computing device described with respect to FIG. 1) with access to a CEWS system and/or an intelligent touch care system (such as the systems described with respect to FIGS. 2 and 3) or by one or more components of the CEWS system and/or intelligent touch care system.

Initially, at step 1102, a touch point for a patient in a community care is received. The touch point may indicate, as shown at step 1104, the patient has a change in a condition to report to a clinician. In response to the touch point, data corresponding to the touch point is communicated, at 1106, to an EHR. At step 1110, data is crawled in the EHR for the patient. The data may include a CEWS that is determined, at least in part, by patient provided data, as shown at step 1108. The patient provided data may be communicated to the EHR before the EHR is crawled, or may be crawled in addition to data being crawled in the EHR.

Based on the touch point and the data in the EHR, a follow-up is initiated, at step 1114, with the clinician. The follow-up may comprise initiating, as shown at step 1116, a telephone clinical assessment. Upon completing the telephone clinical assessment, as shown at step 1118, a second follow-up is determined to be needed. The second follow-up may comprise a video visit. At step 1120, the video visit between the patient and the clinician is initiated. During the video visit, as shown at step 1122, a recommendation may be provided by the intelligent touch care system to the clinician performing the video visit to address the change in the condition of the patient. A third follow-up may be scheduled, at step 1124. The third follow-up may include a second video visit.

At step 1128, the video visit is initiated. Upon the clinician performing the second video visit, it is determined, at step 1130, whether the change in the condition of the patient has been resolved. Upon determining the change in the condition of the patient has been resolved, as shown at step 1132, a second touch point is generated. The second touch point indicates the change in the condition of the patient has been resolved.

Upon determining the change in the condition of the patient has not been resolved, as shown at step 1138, a fourth follow-up is triggered, at step 1138. The fourth follow-up may comprise an in-person visit. The fourth follow-up is scheduled, at step 1142. Upon completing the fourth follow-up or receiving an indication a new order has been provided for the patient, as shown at step 1144, a fifth follow-up may be triggered, at step 1146. The fifth follow-up may be an electronic assessment to be completed by the patient. After receiving an indication the electronic assessment has been completed, at step 1148, it is determined whether an issue corresponding to the change in the condition of the patient has been resolved, at step 1150. Upon determining the issue corresponding to the change in the condition of the patient has been resolved, at step 1152, a second touch point indicating the conditions of the patient has been resolved is generated. Upon determining the issue corresponding to the change in the condition of the patient has not been resolved, at step 1154, a fifth follow-up is scheduled. The fifth follow-up may comprise a video visit, an in-person visit, or a clinician visit. Accordingly, at step 1156, a second touch point is generated for the patient that schedules the fifth follow-up and initiates any corresponding workflow.

Figure 12:
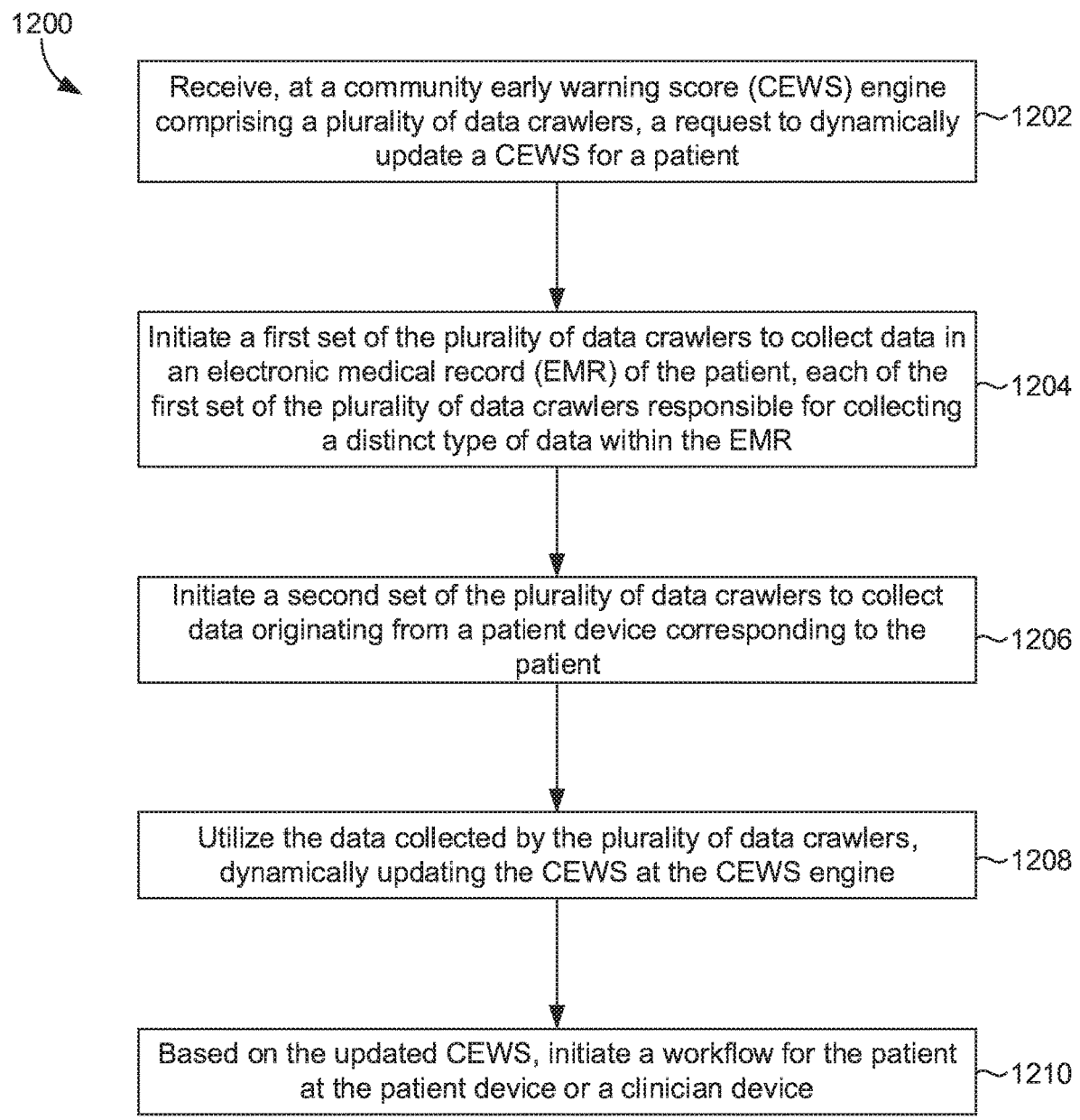
FIG. 12 is a flow diagram of a method illustrating dynamically updating a CEWS, in accordance with embodiments of the present invention.

In FIG. 12, a flow diagram of a method illustrating dynamically updating a CEWS is depicted, in accordance with embodiments of the present invention. Method 1200 may be performed by any computing device (such as computing device described with respect to FIG. 1) with access to a CEWS system and/or an intelligent touch care system (such as the systems described with respect to FIGS. 2 and 3) or by one or more components of the CEWS system and/or intelligent touch care system.

Initially, as shown at step 1202, a request to dynamically update a CEWS for a patient is received at a CEWS engine (e.g., CEWS engine of FIG. 2) comprising a plurality of data crawlers (e.g., initial index component 220, clinical risk factors component 222, SDOH risk profile component 224, clinical risk profile score component 226, biometrics component 228, symptomatology component 230, or clinical assist component 232 of FIG. 2.). The request may be made periodically, based on a touchpoint, based on an update provided by or a request made by a patient device (e.g., patient device 240 of FIG. 2 or 314 of FIG. 3), clinician device (e.g., 316 of FIG. 3), ITC engine 306 (e.g., ITC engine 306 of FIG. 3), or another clinical system.

At step 1204, a first set of the plurality of data crawlers is initiated by CEWS engine to collect data in an EHR of the patient. Each of the first set of the plurality of data crawlers is responsible for collecting a distinct type of data within the EHR. A second set of the plurality of data crawlers is initiated, at step 1206, by CEWS engine to collect data originating from a patient device corresponding to the patient. In embodiments, the plurality of data crawlers may comprise an initial index component, a clinical risk factors component, a social determinants of health (SDOH) risk profile component, a clinical risk profile score component, a biometrics component, symptomatology component, and a clinical assist component. The initial index component may collect facility biometric data and assessment data from the EHR or the patient device to calculate the National Early Warning Score 2 for the patient. The assessment data may include respiratory rate, an estimate of arterial oxygen saturation, hypercapnia, supplemental oxygen, systolic blood pressure, heart rate, level of consciousness, or temperature. The clinical risk factors component may collect medical history and medication profile from the EHR or the patient device to determine clinical risk factors of the patient. The clinical risk factors may include a body mass index of the patient and an indication if the patient is: an opioid risk, an amputee, utilizes a medicinal sleep aid, paraplegic or quadriplegic, has a recent acute admission, or polychronic or polypharmacy. The SDOH risk profile component may collect assessment data and risk assessments from the EHR or the patient device to determine a SDOH risk profile of the patient. The SDOH risk profile may comprise various factors corresponding to the patient including current housing situation of the patient, transportation available to the patient, utilities available to the patient, a financial situation of the patient, a health literacy of the patient, modes of communication available to the patient, social engagement of the patient, stress of the patient, or food insecurity of the patient. The clinical risk profile score component may collect risk assessments from the EHR or the patient device to determine a clinical risk profile score. The clinical risk profile score may comprise risks corresponding to pain, fall, depression, anxiety, dyspnea, Activities of Daily Living/Instrumental Activities of Daily Living, frail or elderly, medication adherence, engagement, confusion, suicide risk, or post-traumatic stress disorder. The biometrics component may collect facility biometric data and assessment data from the EHR or the patient device to determine biometrics for the patient. The biometrics may comprise temperature, heart rate, systolic blood pressure, diastolic blood pressure, mean arterial blood pressure, weight, glucose data, supplemental oxygen, an estimate of arterial oxygen saturation, respiratory rate, activity data, or sleep data. The symptomatology component may collect assessments from the EHR or the patient device to determine symptomology for the patient. The symptomatology may comprise assessed symptoms. The clinical assist component may collect facility biometric data from the EHR or the patient device to determine clinical assist mechanisms associated with the patient. The clinical assist mechanisms may comprise an indication the patient is on: oxygen, infusion, a particular nutrition plan, dialysis, chemotherapy, radiation, or assistive devices. Additionally or alternatively, the plurality of crawlers may collect data derived from a symptom diary of the patient, biometric data from a device owned or utilized by the patient, biometric data from a prescribed kit, caregiver risk assessments, a patient schedule, or personal data of the patient At step 1208, utilizing the data collected by the plurality of data crawlers, the CEWS is dynamically updated at the CEWS engine. Based on the updated CEWS, a workflow for the patient may be initiated, at step 1210, at the patient device or a clinician device (e.g., such as any of the workflows described herein with respect to the ITC engine).

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more computer storage media having computer-executable instructions embodied thereon that, when executed by a computer, causes the computer to perform operations, the operations comprising:
   receiving, at a community early warning score (CEWS) engine comprising a plurality of data crawlers, a request to dynamically update a CEWS for a patient;
   automatically initiating a first set of the plurality of data crawlers to collect data in an electronic health record (EHR) of the patient, each of the first set of the plurality of data crawlers being responsible for collecting a distinct type of data within the EHR;
   automatically initiating a second set of the plurality of data crawlers to collect data originating from a patient device corresponding to the patient;
   utilizing the data collected by the plurality of data crawlers, dynamically updating the CEWS at the CEWS engine; and
   based on the updated CEWS, initiating a workflow for the patient at the patient device or a clinician device.

2. The media of claim 1, wherein the plurality of data crawlers comprise an initial index component, a clinical risk factors component, a social determinants of health (SDOH) risk profile component, a clinical risk profile score component, a biometrics component, symptomatology component, or a clinical assist component.

3. The media of claim 2, wherein the initial index component collects facility biometric data and assessment data from the EHR or the patient device to calculate the National Early Warning Score 2 for the patient, the assessment data including respiratory rate, an estimate of arterial oxygen saturation, hypercapnia, supplemental oxygen, systolic blood pressure, heart rate, level of consciousness, or temperature.

4. The media of claim 2, wherein the clinical risk factors component collects medical history and medication profile from the EHR or the patient device to determine clinical risk factors of the patient, the clinical risk factors including a body mass index of the patient and an indication if the patient is: an opioid risk, an amputee, utilizes a medicinal sleep aid, paraplegic or quadriplegic, has a recent acute admission, or polychronic or polypharmacy.

5. The media of claim 2, wherein the SDOH risk profile component collects assessment data and risk assessments from the EHR or the patient device to determine a SDOH risk profile of the patient, the SDOH risk profile comprising various factors corresponding to the patient including current housing situation of the patient, transportation available to the patient, utilities available to the patient, a financial situation of the patient, a health literacy of the patient, modes of communication available to the patient, social engagement of the patient, stress of the patient, or food insecurity of the patient.

6. The media of claim 2, wherein the clinical risk profile score component collects risk assessments from the EHR or the patient device to determine a clinical risk profile score, the clinical risk profile score comprising risks corresponding to pain, fall, depression, anxiety, dyspnea, Activities of Daily Living/Instrumental Activities of Daily Living, frail or elderly, medication adherence, engagement, confusion, suicide risk, or post-traumatic stress disorder.

7. The media of claim 2, wherein the biometrics component collects facility biometric data and assessment data from the EHR or the patient device to determine biometrics for the patient, the biometrics comprising temperature, heart rate, systolic blood pressure, diastolic blood pressure, mean arterial blood pressure, weight, glucose data, supplemental oxygen, an estimate of arterial oxygen saturation, respiratory rate, activity data, or sleep data.

8. The media of claim 2, wherein the symptomatology component collects assessments from the EHR or the patient device to determine symptomology for the patient, the symptomatology comprising assessed symptoms.

9. The media of claim 2, wherein the clinical assist component collects facility biometric data from the EHR or the patient device to determine clinical assist mechanisms associated with the patient, the clinical assist mechanisms comprising an indication the patient is on: oxygen, infusion, a particular nutrition plan, dialysis, chemotherapy, radiation, or assistive devices.

10. The media of claim 1, wherein the plurality of crawlers collect data derived from a symptom diary of the patient, biometric data from a device owned or utilized by the patient, biometric data from a prescribed kit, caregiver risk assessments, a patient schedule, or personal data of the patient.

11. The media of claim 1, wherein the request is a periodic request, based on a touchpoint, based on an updated provided by or a request made by the patient device, the clinician device, or a clinical system.

12. A computerized method comprising:
receiving, at a community early warning score (CEWS) engine comprising a plurality of data crawlers, a request to dynamically update a CEWS for a patient;
automatically initiating a first set of the plurality of data crawlers to collect data in an electronic health record (EHR) of the patient, each of the first set of the plurality of data crawlers being responsible for collecting a distinct type of data within the EHR;
utilizing the data collected by the plurality of data crawlers, dynamically updating the CEWS at the CEWS engine; and
based on the updated CEWS, initiating a workflow for the patient at the patient device or a clinician device.

13. The method of claim 12, further comprising initiating a second set of the plurality of data crawlers to collect data originating from a patient device corresponding to the patient.

14. The method of claim 13, wherein the second set of the plurality of data crawlers collects data derived from a symptom diary of the patient, biometric data from a device owned or utilized by the patient, biometric data from a prescribed kit, caregiver risk assessments, a patient schedule, or personal data of the patient.

15. The method of claim 12, wherein the request is based on a touchpoint corresponding to a clinician documented change in condition or order.

16. The method of claim 12, wherein the request is based on a touchpoint corresponding to an unscheduled clinician visit.

17. The method of claim 12, wherein the request is based on a touchpoint corresponding to a scheduled clinician visit.

18. The method of claim 12, wherein the request is based on a touchpoint corresponding to a patient question.

19. The method of claim 12, wherein the request is based on a touchpoint corresonding to a patient reporting a change in condition.

20. A system comprising:
a processor; and
a computer storage medium storing computer-usable instructions that, when used by the processor, cause the processor to:
receive, at a community early warning score (CEWS) engine comprising a plurality of data crawlers, a request to dynamically update a CEWS for a patient;
automatically initiate a first set of the plurality of data crawlers to collect data in an electronic health record (EHR) of the patient, each of the first set of the plurality of data crawlers responsible for collecting a distinct type of data within the EHR;
automatically initiate a second set of the plurality of data crawlers to collect data originating from a patient device corresponding to the patient;
utilizing the data collected by the plurality of data crawlers, dynamically update the CEWS at the CEWS engine; and
based on the updated CEWS, initiate a workflow for the patient at the patient device or a clinician device.

* * * * *

UNITED STATES PATENT AND TRADEMARK OFFICE
CERTIFICATE OF CORRECTION

PATENT NO.       : 11,250,959 B2
APPLICATION NO.  : 16/236835
DATED            : February 15, 2022
INVENTOR(S)      : Brown et al.

It is certified that error appears in the above-identified patent and that said Letters Patent is hereby corrected as shown below:

On the Title Page

• Column 2, Line 5, (item (56) Other Publications) - Delete "2018))" and insert -- 2018) --.

In the Drawings

• Sheet 10 of 12, (Reference numeral 1008), (FIG. 10) - Delete "prvoided" and insert -- provided --.
• Sheet 10 of 12, (Reference numeral 1016), (FIG. 10) - Delete "Consumber" and insert -- Consumer --.
• Sheet 10 of 12, (Reference numeral 1018), (FIG. 10) - Delete "Follow" and insert -- Follow-up --.

In the Specification

• Column 7, Line 47-48, - Delete "Electronic" and insert -- Electronics --.
• Column 15, Line 9, - Delete "tot eh" and insert -- to the --.
• Column 17, Line 17, - Delete "10002." and insert -- 1002. --.
• Column 20, Line 5, - After "patient" insert -- . --.

In the Claims

• Column 21, Line 50, - In Claim 11, delete "updated" and insert -- update --.
• Column 22, Line 32, - In Claim 19, delete "corresonding" and insert -- corresponding --.

Signed and Sealed this
Seventeenth Day of May, 2022

Katherine Kelly Vidal
*Director of the United States Patent and Trademark Office*